United States Patent
Galvez et al.

(10) Patent No.: US 11,941,161 B2
(45) Date of Patent: Mar. 26, 2024

(54) DATA MANIPULATION USING REMOTE AUGMENTED SENSING

(71) Applicant: Augmental Technologies Inc., San Francisco, CA (US)

(72) Inventors: Tomas Alfonso Vega Galvez, San Francisco, CA (US); Corten Singer, San Francisco, CA (US)

(73) Assignee: Augmental Technologies Inc., San Francisco, CA (US)

( * ) Notice: Subject to any disclaimer, the term of this patent is extended or adjusted under 35 U.S.C. 154(b) by 0 days.

(21) Appl. No.: 17/366,186

(22) Filed: Jul. 2, 2021

(65) Prior Publication Data

US 2022/0004251 A1 Jan. 6, 2022

Related U.S. Application Data

(60) Provisional application No. 63/162,444, filed on Mar. 17, 2021, provisional application No. 63/063,455, filed on Aug. 10, 2020, provisional application No. 63/047,946, filed on Jul. 3, 2020.

(51) Int. Cl.
*H04W 4/38* (2018.01)
*G06F 3/01* (2006.01)

(52) U.S. Cl.
CPC .............. *G06F 3/011* (2013.01); *G06F 3/017* (2013.01); *H04W 4/38* (2018.02); *G06F 3/016* (2013.01)

(58) Field of Classification Search
CPC .......... G06F 3/011; G06F 3/017; G06F 3/016; G06F 2203/0384; H04W 4/38; A61F 4/00
See application file for complete search history.

(56) References Cited

U.S. PATENT DOCUMENTS

| | | | |
|---|---|---|---|
| 6,613,001 B1 * | 9/2003 | Dworkin | A61C 7/00 600/590 |
| 8,812,096 B2 | 8/2014 | Flaherty et al. | |
| 10,137,363 B2 | 11/2018 | Parshionikar | |
| 10,234,938 B2 | 3/2019 | Moffat et al. | |
| 10,542,929 B2 | 1/2020 | Kimmel | |
| 10,600,417 B2 | 3/2020 | Tormasov et al. | |
| 2012/0299826 A1 * | 11/2012 | Moeller | G10L 25/75 345/158 |
| 2013/0090931 A1 * | 4/2013 | Ghovanloo | A61F 4/00 704/275 |

(Continued)

*Primary Examiner* — Ryan F Pitaro
(74) *Attorney, Agent, or Firm* — Adams Intellex, PLC

(57) ABSTRACT

Data manipulation using remote augmented sensing is disclosed. Wireless connectivity is provided between a processor and a wireless transceiver. The wireless transceiver is embedded in an oral sensing interface. A tongue position sensor (TPS) is coupled to the wireless transceiver. The tongue position sensor is attached to the interface. An inertial measurement unit (IMU) is coupled to the wireless transceiver. The IMU is attached to a location along the interface. An interface-embedded preprocessor is further coupled between the wireless transceiver and the output from the TPS and the IMU. Data manipulation is enabled in the processor, based on the wireless connectivity and outputs from the TPS and the IMU. Other sensors are coupled, including a barometric sensor, an ambient condition sensor, a microphone, and a sound generating device. At least one additional inertial measurement unit is coupled to the wireless transceiver.

30 Claims, 8 Drawing Sheets

(56) References Cited

U.S. PATENT DOCUMENTS

| | | | |
|---|---|---|---|
| 2015/0346840 A1* | 12/2015 | Alonaizi | G06F 3/0233 |
| | | | 345/169 |
| 2016/0000548 A1* | 1/2016 | Aiden | A61F 5/0013 |
| | | | 623/23.72 |
| 2016/0117940 A1 | 4/2016 | Gomory et al. | |
| 2016/0125705 A1* | 5/2016 | Hurtig | G16H 40/63 |
| | | | 340/4.11 |
| 2016/0154468 A1* | 6/2016 | Kimmel | G08C 17/02 |
| | | | 345/156 |
| 2016/0367188 A1 | 12/2016 | Malik et al. | |
| 2017/0061784 A1* | 3/2017 | Clough | G06F 3/04842 |
| 2018/0300008 A1 | 10/2018 | Rasanen | |
| 2019/0004596 A1* | 1/2019 | Henrique Barbosa Postal | |
| | | | H04W 4/80 |
| 2019/0041975 A1* | 2/2019 | Anderson | A61B 5/381 |
| 2019/0302894 A1* | 10/2019 | Alvarado | A61F 4/00 |
| 2020/0375528 A1* | 12/2020 | Flanagan | A61B 5/087 |
| 2021/0085247 A1* | 3/2021 | Meirav | A61B 5/083 |
| 2021/0256246 A1* | 8/2021 | Dagdeviren | G06V 40/174 |
| 2022/0004251 A1* | 1/2022 | Vega Gálvez | H04W 4/38 |
| 2022/0223247 A1* | 7/2022 | Davidson | A61B 5/4845 |
| 2023/0102363 A1* | 3/2023 | Mehring | A61F 4/00 |
| | | | 345/156 |

\* cited by examiner

500

| SENSOR | OUTPUT | STATE | ACTION |
|---|---|---|---|
| MICROPHONE | AUDIO SIGNAL | MONITORING | PREPROGRAMMED |
| BAROMETRIC | TRI-VALUE STATE AND/OR CONTINUOUS | AMBIENT BAROMETRIC PRESSURE | NEUTRAL |
| | | POSITIVE BAROMETRIC PRESSURE | EXHALE INTO CLOSED ORAL CAVITY |
| | | NEGATIVE BAROMETRIC PRESSURE | INHALE FROM CLOSED ORAL CAVITY |
| | | BAROMETRIC PRESSURE CHANGE | TONGUE PRESSES; TONGUE/MOUTH SUCTION |

502

| SENSOR | OUTPUT | STATE |
|---|---|---|
| AMBIENT CONDITIONS | BIOMETRIC DATA CHANGE | TEMPERATURE |
| | | HEARTRATE |
| | | HYDRATION |
| | | pH |
| | | OXYGEN (O2 SAT) |
| | | MICROBIAL/ENZYME |
| | | HORMONE |
| | | BLOOD PRESSURE |
| | | CLENCHING FORCE |
| | | AIRFLOW |

*FIG. 5A*

DATA MANIPULATION USING REMOTE AUGMENTED SENSING

RELATED APPLICATIONS

This application claims the benefit of U.S. provisional patent applications "Data Manipulation Using Remote Augmented Sensing" Ser. No. 63/047,946, filed Jul. 3, 2020, "Gestural Sensing Using In-Ear Inertial Measurements" Ser. No. 63/063,455, filed Aug. 10, 2020, and "Intraoral Connected Processing Devices" Ser. No. 63/162,444, filed Mar. 17, 2021.

Each of the foregoing applications is hereby incorporated by reference in its entirety.

FIELD OF ART

This application relates generally to data manipulation and more particularly to data manipulation using remote augmented sensing.

BACKGROUND

People have a passion for their many electronic devices. With the possible exceptions of water sports, bathing, and sleeping, people are rarely far from their favorite gadgets. The gadgets are used for communicating; performing work related tasks such as drafting documents, spreadsheets, and presentations; engaging in educational tasks such as classes, tutorials, recitations, and laboratories; performing research tasks such as data collection and analysis; among myriad other uses. The uses further include consuming a wide variety of online content such as politics, news updates, sports scores, and other items of import, interest, amusement, and diversion. Other uses often further include consuming video streams such as TV programs, movies, adorable puppy and kitten videos, children doing silly things videos, and streaming provided by Internet influencers, each stream intended to provide entertainment and occasionally useful information to the user. The gadgets are also used for keeping in touch with family, friends, coworkers, and other people through email, chat, social media, photos, and even telephony. The ways by which a user employs an electronic device to consume media or to engage with others depend on the particular device. Smartphones are delightfully portable, enabling usage while a person is out and about, traveling, or staying in for a quiet night at home. A smartphone can access the Internet; connect to news, information, and social media sites; enable online shopping; and support email, chatting, and calls; among seemingly countless other uses.

One distinct disadvantage of a device such as a smartphone is that the smartphone display screen is comparatively small. Typically, only a few inches in diagonal dimension, text can be small and hard to read. Further, media developed for "the big screen" such as movies, or even media produced for a television screen, can be difficult to watch and enjoy due to the small proportions. By comparison, a tablet device offers much of the portability of the smartphone with the favorable advantage of a larger display. The larger display of the tablet device makes interactions with others more enjoyable because the larger display enables better viewing of other people engaged in the interaction. Further, the larger display greatly enhances media streaming by enlarging people, building, places, vehicles, etc., within the streamed media. A laptop device such as a laptop computer is less portable than the smartphone or the tablet devices, but provides a yet larger display. The laptop device can access the Internet, interact with others, and engage in many other popular uses. The laptop further offers the distinct advantage in that its more powerful processors are far better suited to more complex uses such as creative activities, learning, working, and research.

SUMMARY

People frequently find themselves in situations where they have to multitask. Tasks such as engaging in a video call while opening a file or initiating a computer search for an answer to a question that came up during the call have become routine. Viewing, talking, typing, mousing, swiping, and similar activities converge to enable and enhance the user experience. There are times, however, when overt interaction by a user with a computing or communication device is socially unacceptable, impossible, dangerous, or even illegal. In such situations, people are engaging in activities that require them to interact with processors while they are performing other tasks. The tasks can engage the user's hands, thus preventing the user from engaging with common input/output devices. In other instances, the user may have physical challenges or limitations which prevent human-machine interactions. These multifaceted requirements of the divergent tasks can include accessing a repair manual while working on a piece of equipment, reading design specifications while operating a machine, or even using augmented reality while performing surgery. In addition, situations exist in which a person cannot use conventional input/output devices or techniques. These latter situations can include low light conditions, limited access to input/output devices, or even covert activities.

Wireless connectivity is provided between a processor and a wireless transceiver. The wireless connectivity can be based on wireless communications such as WiFi™, Bluetooth™, Zigbee™, near field communications (NFC), cellular, and so. The wireless connectivity can provide communications over distances ranging from a few millimeters, to centimeters, to meters, and so on. A tongue position sensor (TPS) is coupled to the wireless transceiver, where the tongue position sensor is attached to the interface. The tongue position sensor can be located above the tongue, below the tongue, to the sides of the mouth, etc. An inertial measurement unit (IMU) is coupled to the wireless transceiver, where the IMU is attached to a location along the interface. The IMU can be used to detect the position, rotation, acceleration, etc., of the user's head. The IMU can detect head gestures such as nods, shakes, tilts, and so on. An interface-embedded barometric sensor is further coupled to the wireless transceiver. The barometric sensor can detect changes in air pressure within a closed space such as an oral cavity. The barometric sensor can detect pressures along a continuum of pressures, that is, not just at specific pressures. However, the barometric sensor can be used to detect a tri-value state of air pressure within the oral cavity containing the interface. The tri-value state includes ambient barometric pressure, increased barometric pressure due to exhaling into a closed oral cavity, and decreased barometric pressure due to inhaling from a closed oral cavity. The tri-value state collected from the barometric sensor modifies the output of the TPS and the IMU. Data manipulation is enabled in the processor, based on the wireless connectivity and outputs from the TPS and the IMU. The data manipulation can include opening and closing files, selecting menu items, data entry, etc. The data manipulation can be based on mouse and trackpad operations such as scrolling, swiping, clicking, double clicking, right clicking, and the like. At least one additional inertial measurement unit can be coupled to the wireless transceiver. The inertial measurement unit and the at least one additional inertial measurement unit are attached to nonadjacent locations along the interface. The nonadjacent locations can include the left and right sides of the mouth, upper and lower jaw, and the like. The enabling data manipulation is augmented by the at least one additional inertial measurement unit. Feedback is provided to a user of the interface. The feedback can include haptic feedback generated by a haptic device, audio feedback generated by a sound generating device, etc.

Disclosed techniques enable data manipulation using remote augmented sensing. Users typically interact with processing devices by typing, clicking, touching, pressing, swiping, and other familiar input/output techniques. At times, however, these techniques cannot be used due to impairments associated with a user. The impairments can include visual impairments, motor impairments, and cognitive impairments that prevent the user from providing input, receiving output, and so on. Other impairments that can be associated with a user include situational impairments. These impairments inhibit or prevent access to or usage of the input/output techniques due to a situation in which the user is trying to interact with the processing device. The situations can include lighting that is too bright or too dark, noisy environments, locations where speaking is not permitted, etc. The situations can also include those in which the user is using their eyes, ears, hands, voice, etc. for another activity.

Data manipulation using remote augmented sensing is disclosed. Wireless connectivity is provided between a processor and a wireless transceiver, wherein the wireless transceiver is embedded in an oral sensing interface. A tongue position sensor (TPS) is coupled to the wireless transceiver, wherein the tongue position sensor is attached to the interface. An inertial measurement unit (IMU) is coupled to the wireless transceiver, wherein the IMU is attached to a location along the interface. An interface-embedded preprocessor is further coupled between the wireless transceiver and the output from the TPS and the IMU. Data manipulation is enabled in the processor, based on the wireless connectivity and outputs from the TPS and the IMU. Other sensors, including a barometric sensor, an ambient condition sensor, and a microphone, can be coupled. At least one additional inertial measurement unit can be coupled to the wireless transceiver. The inertial measurement unit and the at least one additional inertial measurement unit are attached to nonadjacent locations along the interface. Feedback is given to a user of the interface. The feedback can include haptic feedback generated by a haptic device attached to the interface. The feedback can further include audio feedback generated by a sound generating device attached to the interface.

Disclosed techniques include a processor-implemented method for data manipulation comprising: providing wireless connectivity between a processor and a wireless transceiver, wherein the wireless transceiver is embedded in an oral sensing interface; coupling a tongue position sensor (TPS) to the wireless transceiver, wherein the tongue position sensor is attached to the interface; coupling an inertial measurement unit (IMU) to the wireless transceiver, wherein the IMU is attached to a location along the interface; and enabling data manipulation in the processor, based on the wireless connectivity and outputs from the TPS and the IMU.

Various features, aspects, and advantages of various embodiments will become more apparent from the following further description.

BRIEF DESCRIPTION OF THE DRAWINGS

The following detailed description of certain embodiments may be understood by reference to the following figures wherein:

FIG. 5A shows sensor usage.

DETAILED DESCRIPTION

Figure 1:
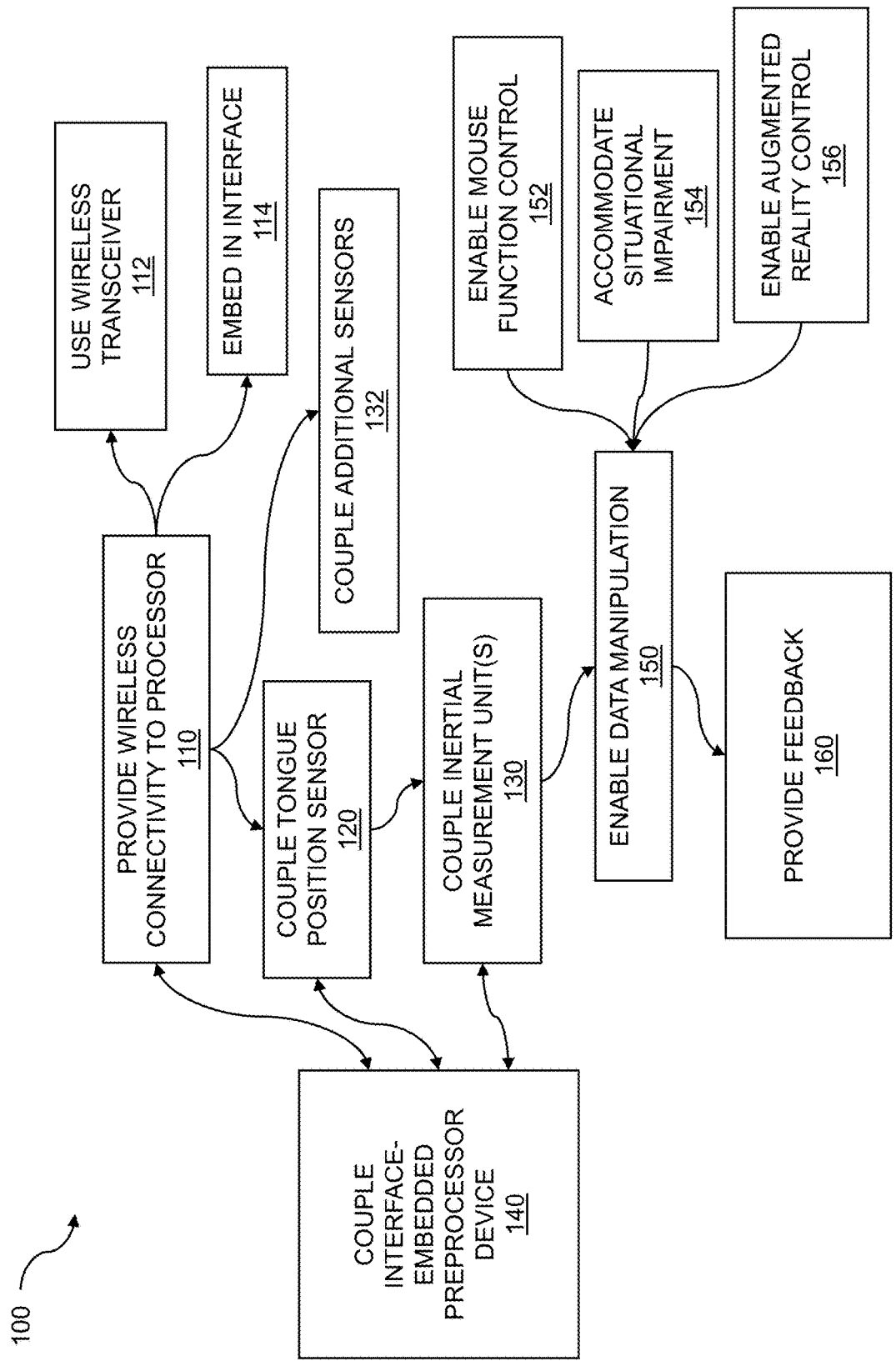
FIG. 1 is a flow diagram for data manipulation using remote augmented sensing.

This disclosure provides techniques for data manipulation using remote augmented sensing. Users employ a diversity of techniques to interact with processors. The processors can include personal electronic devices such as smartphones, tablets, and personal digital assistants (PDAs); laptop and desktop computers; servers, whether local or cloud-based; and so on. The techniques by which users interact with processors can be based on typing on a keyboard, moving and clicking a mouse, swiping and tapping or pressing a trackpad, speaking into a microphone, reading contents of a display, and so on. However, use of these typical input/output techniques for user-processor interaction is not always possible. One or more impairments can be associated with a particular user. Motor impairments can prevent a user from typing and controlling a mouse or trackpad, visual impairments can prevent a user from reading a display, and so on. Other impairments can include situational impairments. A situational impairment, which can impede or prevent a user from employing common input/output techniques, is based on a user's situation. A situational impairment can include a bright light environment in which a user cannot read a display, a low light situation preventing use of a keyboard, and the like. Situational impairments can also be based on circumstances of the user for which speaking violates rules or social mores, accessing a screen is deemed rude, and the like. Further situations can include the user being engaged in another activity such as machine operation or surgery. In these latter cases, the user is unable to access a keyboard, mouse, or trackpad because the user's hands are otherwise occupied.

In disclosed techniques, data manipulation uses remote augmented sensing. The augmented sensing is implemented for processor-based data manipulation using an oral sensing interface. Wireless connectivity is provided between a processor and a wireless transceiver. The wireless transceiver is embedded in the oral sensing interface. A tongue position sensor (TPS) is coupled to the wireless transceiver, where the tongue position sensor is attached to the interface. Inertial measurement units (IMUs) are coupled to the wireless transceiver. The IMUs are attached to non-adjacent locations of the interface. Data manipulation is enabled within the processor. The enabling is based on the wireless connectivity and output from the TPS and the IMUs. Feedback in the form of both haptic feedback and audio feedback is provided to the interface user.

Some embodiments include a processor-implemented method for data manipulation comprising: providing wireless connectivity between a processor and a wireless transceiver, wherein the wireless transceiver is embedded in an oral sensing interface; coupling a tongue position sensor (TPS) to the wireless transceiver, wherein the tongue position sensor is attached to the interface; coupling an inertial measurement unit (IMU) to the wireless transceiver, wherein the inertial measurement unit is attached to the interface; and enabling data manipulation in the processor, based on the wireless connectivity and output from the TPS and the IMU. In embodiments, the IMU is embedded in an inferior dental arch location for the oral sensing interface. Thus, for oral sensing interfaces located in the inferior dental arch, that is, in the lower jaw dental cavity, the additional movement potential of the lower jaw vis a vis the upper jaw can enable interface functionality using a single IMU. The inferior dental arch can express three-dimensional movement with greater degrees of freedom and magnitude than can the superior dental arch, and therefore its range of motion can be exploited using only one IMU.

FIG. 1 is a flow diagram for data manipulation using remote augmented sensing. A user may operate various sensors to enable data manipulation in a processor while they are experiencing situational impairment. Situational impairment can refer to a user's inability to interact with a computer, processor, and so on, due to their situation. The flow 100 includes providing wireless connectivity 110 between a processor and a wireless transceiver. The wireless connectivity can be based on communications standards, preferred protocols, low power techniques, and so on. The wireless connectivity can be based on the 802.11 family or "Wi-Fi™", Bluetooth™, Zigbee™, and so on. The wireless connectivity can be based on near field communication (NFC). The wireless connectivity can be based on near field magnetic induction (NFMI). The wireless connectivity can be provided as part of a wireless personal area network (WPAN). The wireless connectivity can be enabled by using a wireless transceiver 112 to implement the desired wireless connectivity. In the flow 100, the wireless transceiver is embedded in an oral sensing interface 114. An oral sensing interface can be worn by a user, placed within the user's oral cavity, and so on. In embodiments, the oral sensing interface can include a retainer or "bite plate". The retainer can be custom fitted to the user in order to enable both proper fit of the interface and comfort of the user. Further embodiments include coupling a battery to the wireless transceiver. The battery can include a replaceable battery, a rechargeable battery, and so on. In other embodiments, the battery is charged wirelessly in a user's oral cavity. In embodiments, the battery is replaced, charged, and/or augmented with a piezoelectric layer included in the oral sensing interface. Natural movements of the jaw can enable electrical energy production during normal jaw movements such as chewing, talking, and the like.

The flow 100 includes coupling a tongue position sensor (TPS) 120 to the wireless transceiver, where the tongue position sensor is attached to the interface. The tongue position sensor can be located such that it can be easily accessible to the tongue. In embodiments, the TPS can be placed below the tongue of the user, such as when the retainer is worn on the lower teeth. An alternative location for the TPS can be above the tongue, such as when the retainer is worn on the upper teeth. The TPS can include electrodes, pressure sensors, optical sensors, ultrasonic sensors, etc. Tongue input data can be detected by the TPS and can augment, control, or modify data collected by, or being processed by, a processor or preprocessor. The tongue input data can be sensed based on tongue position, tongue pressure, tongue movement, tongue movement direction, tongue movement speed, tongue movement acceleration, and so on.

The flow 100 includes coupling one or more inertial measurement units (IMUs) 130 to the wireless transceiver. If more than one IMU is deployed, they can be attached to non-adjacent locations of the interface. An example placement of the IMUs is discussed below, where the IMUs are located along the left and the right sides of a retainer comprising the oral sensing interface. The IMU can be used to detect tongue or jaw positions, rotation, acceleration, and so on. Having more than one IMU coupled to the interface can enable additional and/or more granular detection of motion and/or movement in an oral cavity. In embodiments, at least one additional inertial measurement unit is coupled to the wireless transceiver. In embodiments, the inertial measurement unit and the at least one additional inertial measurement unit are attached to nonadjacent locations along the interface. And in embodiments, the enabling data manipulation is augmented by the at least one additional inertial measurement unit. As described below, the flow 100 includes coupling additional sensors 132 to the wireless transceiver.

The flow 100 further includes coupling an interface-embedded preprocessor device 140 to the wireless transceiver to augment the enabling data manipulation. The preprocessor can be used to process data collected from the TPS, IMU(s), and other coupled devices. The processing of the preprocessor can include noise reduction, filtering, conversion from analog signals to digital signals, mapping sensor data to a value using a technique such as a lookup table, etc. The processing of the preprocessor can also include application processing, such as running code to determine status of the user, health of the user, direction or instruction from the user, etc. In embodiments, the preprocessor device includes wireless transceiver functionality. The wireless transceiver can send to and receive data from an electronic device which is accessible to the user, adjacent to the user, worn by the user, and so on.

The flow 100 includes enabling data manipulation 150 in the processor, based on the wireless connectivity and output from the TPS and the IMU. The data manipulation can include opening, executing, and closing applications; accessing files for reading and writing; and so on. The enabling data manipulation can be based on opening and closing windows, providing data and other inputs to the processor, receiving results or other communications from the processor, and so on. The data manipulation in the processor can enable a diversity of applications, assistive technologies, immersive technologies, and the like. In embodiments, the TPS can enable oral mouse function control 152. Mouse function control can include moving a cursor, clicking, and so on. In embodiments, the oral mouse function control includes mouse function detection, such as mouse movement, mouse swipes, mouse clicks, mouse double-clicks, and mouse wheel control. Further mouse functions, such as secondary functions, can be based on an amount of pressure exerted by the tongue on the TPS. In embodiments, the data manipulation can be targeted for one or more Internet of Things (IoT) devices. Such data manipulation can potentially enable control of any Internet-connected device using remote augmented sensing, and in particular, oral remote augmented sensing.

In the flow 100, the data manipulation is used to accommodate situational impairment 154 experienced by a person. The impairments can include visual, motor, and cognitive impairments. In embodiments, the sensor-based data manipulation enablement can be used to accommodate severe motor impairment in a person, which can limit or prevent the person from accessing a processor using conventional devices such as keyboards, mice, trackpads, monitors, and so on. Different from visual, motor, or cognitive impairments, situational impairments occur when a user is not able to use processors and devices because of their situation. Such situations can occur due to ambient conditions such as too much light to read a screen or too little light to use a keyboard or trackpad; too loud an environment to hear audio feedback from the processor or computing device; too little ambient noise where speaking would disturb others such as in a library or at a movie; etc. Other causes of situational impairment can include an inability to use standard input/output devices when it is socially unacceptable; when a user's hands, eyes, and voice are otherwise occupied; and when covert interaction with a processor is required. Some situational impairments can be associated with a particular user due to their physiological, mental, or emotional situation. For example, motor impairments can prevent a user from typing and controlling a mouse or trackpad; visual impairments can prevent a user from reading a display; and so on. In embodiments, the situational impairment accommodation can enable control of a joystick functionality without having hand motor skills to control it traditionally. Examples can include operating a wheelchair or controlling another vehicle type.

In embodiments, the situational impairment can include operating a machine. The machine can generate too much noise to hear audio feedback or to provide voice commands, can require two hands to operate, and the like. In further embodiments, the situational impairment can include performing a surgical procedure. In the flow 100, the data manipulation is used to provide input for an augmented reality control system 156 used by a person. Augmented reality can include enhancing or "augmenting" a real life experience by adding content to the experience. The augmenting can include superimposing images, text, icons, etc., onto a view of the real world. In a usage example, augmented reality can include superimposing travel instructions onto the real world view, displaying information about a person you met on the street, highlighting the objective of a surgery, and so on.

The flow 100 includes providing feedback 160 to a user of the interface. The feedback that is provided to the user of the interface can include results of data manipulation enabled in the processor, alerts, warnings, codes, and so on. In embodiments, the feedback can include haptic feedback generated by a haptic device attached to the interface. The haptic feedback can include vibration, pressure, a tingling sensation, and the like. In other embodiments, the feedback can include audio feedback generated by a sound generating device attached to the interface. The sound generating device can include a speaker, a transducer, and so on. In embodiments, the sound generating device can use jawbone structure for audio propagation. Other feedback forms, such as electrical stimulation, are possible and can be used with haptic and/or audio feedback or by themselves.

Continuing with feedback, in embodiments, the feedback can originate in the processor and can be transmitted to the interface using the wireless connectivity. The wireless connectivity can be based on the various wireless techniques discussed throughout. In other embodiments, the feedback can originate in the processor and can be based on output previously received by the processor over a connection using the wireless connectivity. The output previously received by the processor can include TPS data, IMU data, data from other sensors that can be coupled to the interface, and the like. The feedback can be based on an action taken by the user. In embodiments, the feedback can be responsive to active oral manipulation by a user of the interface. The active oral manipulation can include the user moving their tongue to move the cursor, click, etc. In embodiments, the active oral manipulation can accomplish data manipulation in the processor. The active oral manipulation can access files for input and output, operate applications, and so on. In further embodiments, the feedback can be responsive to passive monitoring of a person using the interface. The passive monitoring can include monitoring the user's health, habits, activities, etc. In embodiments, the feedback can be used to control bruxism in the user. Bruxism, or "teeth grinding", can be quite harmful to the teeth. In other embodiments, the feedback can be used to control sleep apnea in the user. Sleep apnea can result from the airway closing off while sleeping. Sleep apnea can manifest as loud snoring, gasping, and so on, and has many undesirable side effects which can include headaches, depression, stroke, or heart failure.

Various embodiments of the flow 100 can be included in a computer program product embodied in a non-transitory computer readable medium that includes code executable by one or more processors.

Figure 2:
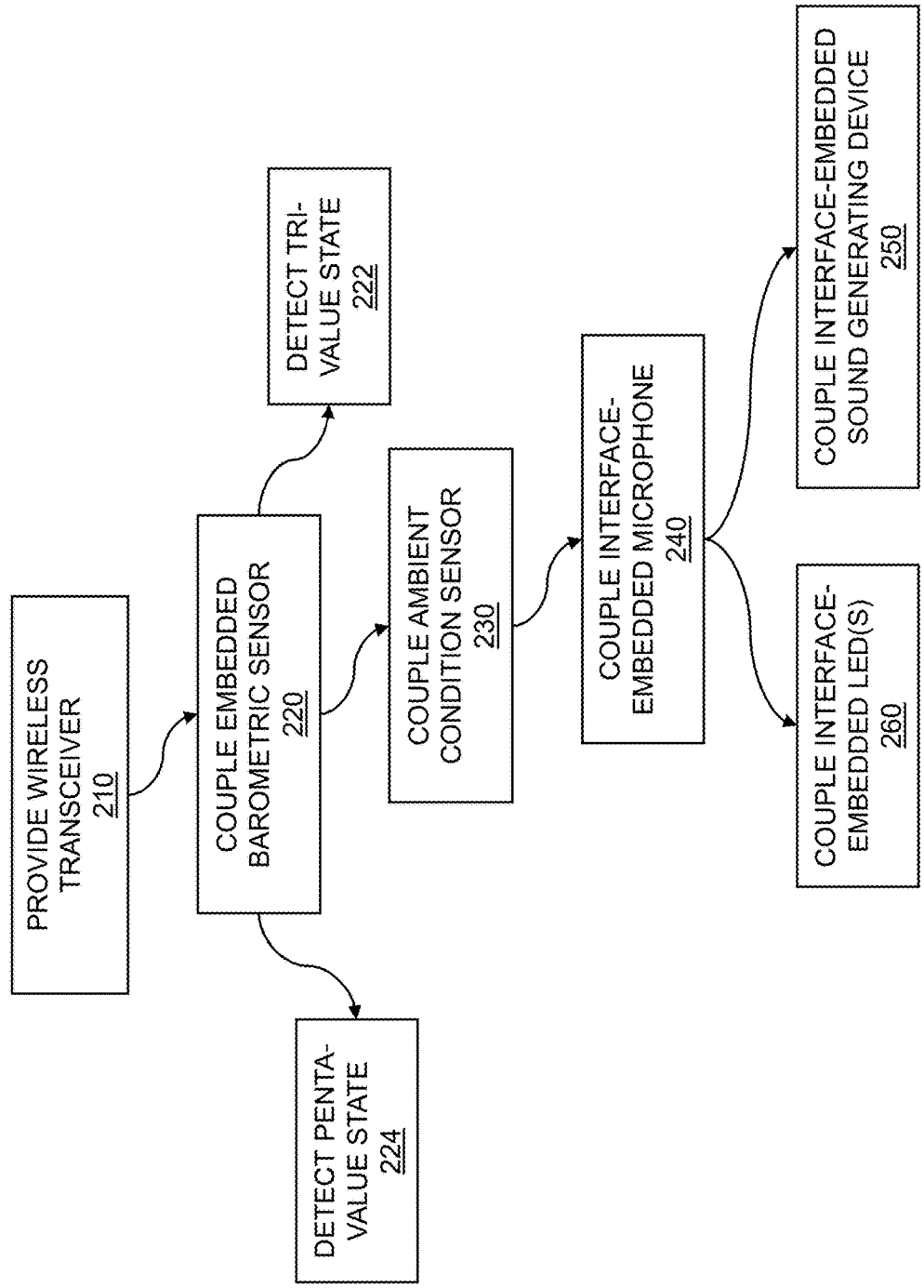
FIG. 2 is a flow diagram for interface-embedded sensors.

FIG. 2 is a flow diagram for interface-embedded sensors. A user-processor interface can be applied by the user to enable data manipulation within the processor. The data manipulation can include opening, operating, and closing applications; selecting data files; writing data files; and so on. The interface can enable the user to operate the processor, execute programs, etc., when the use of "standard" interfaces such as keyboards, mice, trackpads, microphones, headphones, etc., is not possible, impractical, socially unacceptable, and so on. These conditions, such as noisy environments, quiet environments (for instance, a library or a courtroom), overly bright or dim environments, etc., contribute to "situational impairment". Situational impairment refers to a situation in which accessing processors, computers, and the like, is difficult, socially unacceptable, imprudent, etc.

The flow 200 includes providing wireless connectivity between a processor and a wireless transceiver 210. The wireless connectivity can be based on a variety of wireless communications technologies such as Wi-Fi™, Bluetooth™, near field communication (NFC), near field magnetic induction (NFMI), Zigbee™, and so on. The wireless connectivity can be provided as part of a wireless personal area network (WPAN). In embodiments, the wireless transceiver is embedded in an oral sensing interface. The oral sensing interface can include a prosthetic such as a retainer that can be placed into a user's oral cavity. The flow 200 includes coupling an interface-embedded barometric sensor 220 to the wireless transceiver. The barometric sensor can be used to detect ambient barometric pressure, changes in barometric pressure such as increases or decreases, and so on. In the flow 200, the barometric sensor detects a tri-value state 222 of air pressure within an oral cavity containing the interface. The tri-value state can include a number, a code, a percentage, text, and the like. The tri-value state can be sensed from a continuum of pressures and can include ambient barometric pressure, increased barometric pressure due to exhaling into a closed oral cavity, and decreased barometric pressure due to inhaling from a closed oral cavity. The barometric sensor can detect a plurality of pressures along an analog or continuum of possible pressures for sensing.

In embodiments, an output of the barometric sensor is used in the enabling data manipulation, either in conjunction with outputs of other sensors or by itself, and it can modify the output of other sensors when included in the oral sensing interface. In further embodiments, the tri-value state can include ambient barometric pressure, increased barometric pressure due to exhaling into a closed oral cavity, and decreased barometric pressure due to inhaling from a closed oral cavity.

In embodiments, the barometric sensor can detect a penta-value state 224. The penta-value state includes five different states that can be detected by the barometric sensor: ambient (nothing or no change), modestly higher pressure (a soft blow of breath into a closed mouth), high pressure (a hard blow of breath into a closed mouth), modestly lower pressure (a soft draw of breath into a closed mouth), and low pressure (a hard draw of breath into a closed mouth). The penta-value state can represent five different values, options, numbers, code words, alphanumeric symbols, punctuations, and so on. In embodiments, the penta-value mode and the tri-value mode can be activated by a mode selection, controlled either by an external processor or an in-mouth processor.

The flow 200 includes coupling an ambient condition sensor 230 to the wireless transceiver. The ambient condition sensor can be used to measure ambient conditions within the oral cavity of a user, ambient conditions outside the oral cavity of the user, etc. In embodiments, the ambient condition sensor includes biometric sensors. The biometric sensors can be used to measure a diversity of biological parameters associated with the user of the oral interface. In embodiments, the biometric sensors can include temperature, heart rate, hydration, pH, oxygen, microbe, hormone, enzyme, blood pressure, jaw clenching force, and airflow sensors. The ambient condition sensor can be used to detect a biological parameter at a point in time. In embodiments, the ambient condition sensor can be responsive to changes in ambient conditions. An ambient condition sensor can include an interface-embedded temperature sensor. The interface-embedded temperature sensor can be used to augment the barometric sensor or other interface-embedded sensors.

The flow 200 includes coupling an interface-embedded microphone 240 to the wireless transceiver. The microphone can further include a pickup, a transducer, or another device that can be used to collect audio data within the oral cavity. The microphone can collect ambient sounds, speech, human-generated sounds, and so on. In embodiments, the microphone enables near-silent speech recognition. The microphone can be used while the user is in a situation where they are not able or permitted to speak out loud. In embodiments, the microphone can be enabled based on an output from an interface-embedded sensor, such as the TPS, the one or more IMUs, and/or other embedded sensors. The microphone can be operated using a "normally off" technique where the microphone can be enabled or turned on based on the TPS or IMU sensors. In other embodiments, the microphone can be enabled based on an output from another interface-embedded sensor. In other embodiments, completely silent communication can be enabled by identifying tongue and/or mouth movements to map words, symbols, or letters to be processed by the disclosed method.

The flow 200 includes coupling an interface-embedded sound generating device 250 to the wireless transceiver. The sound generating device can comprise a bone-conduction sound generating device or speaker. The bone-conduction speaker can deliver audio frequency soundwaves directly to the jaw structure through attachment to a tooth, coupling through the interface, through soft tissue in proximity to the bone, and so on. The sound generating device can be used to provide feedback to a user of the interface. The flow 200 includes coupling one or more light-emitting diodes (LEDs) 260 to the wireless transceiver. The one or more LEDs can be used to provide visible feedback to a user or others with whom a user comes in contact. The LEDs can be sensed by an external device, such as a smartphone, such that proper installation, initialization, and/or operation of the interface can be confirmed. A smartphone or other device with a camera can be held in front of a user's open mouth to detect LED activity. In some embodiments, the LED activity is detectible through the soft tissue enclosing a user's oral cavity. In some embodiments, the wavelength(s) of light emitted by the LED(s) falls outside of the visible light spectrum. In other embodiments, the LED activity primarily serves an entertainment or marketing kind of purpose, such as giving a user the ability to perform her own in-mouth light show.

Various embodiments of the flow 200 can be included in a computer program product embodied in a non-transitory computer readable medium that includes code executable by one or more processors.

Figure 3:
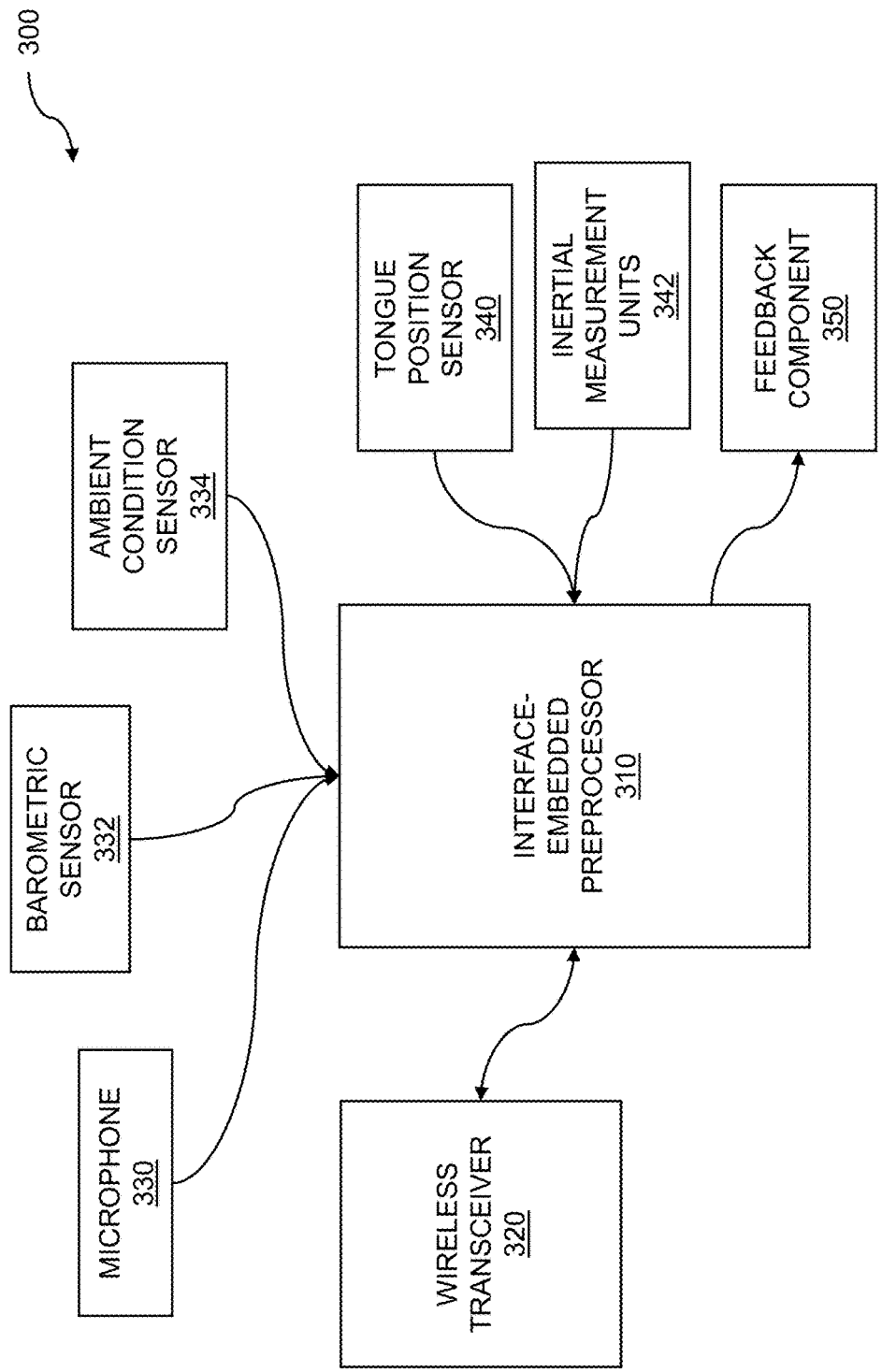
FIG. 3 is a system block diagram for remote augmented sensing.

FIG. 3 is a system block diagram for remote augmented sensing. A tongue position sensor, inertial measurement units, biometric sensors, and so on, can be used to collect data from and process data for a user. The data collecting and processing enables data manipulation using remote augmented sensing. Wireless connectivity is provided between a processor and a wireless transceiver. The wireless transceiver is embedded in an oral sensing interface. A tongue position sensor (TPS) is coupled to the wireless transceiver, and an inertial measurement unit (IMU) is coupled to the wireless transceiver. A barometric sensor is coupled to the wireless transceiver. An additional inertial measurement unit is attached to a nonadjacent location of the interface and coupled to the wireless transceiver. Data manipulation is enabled in the processor, based on the wireless connectivity and outputs from the sensors. Data manipulation is augmented by a preprocessor coupled to the wireless transceiver.

A system block diagram for remote augmented sensing is shown 300. The system block diagram can include an interface-embedded preprocessor 310. The interface-embedded preprocessor can process data collected from a variety of sensors. Embodiments can include coupling an interface-embedded preprocessor between the wireless transceiver and the output from the TPS and the IMU. The preprocessor can be used to calibrate, filter, convert, or otherwise handle data collected from the TPS and the IMUs. The preprocessor can offload any or all processing requirements from the wirelessly connected processor. The preprocessor can enable the wirelessly connected processor to be disconnected for periods of time. The system block diagram can include a wireless transceiver 320. The wireless transceiver can include a transmitter/receiver pair (TX/RX), where the wireless transceiver can enable two-way data transfer between an external device and interface-embedded devices coupled to the transceiver, including the interface-embedded preprocessor. The external device can include a computer or processor, a smart device such as a smartphone or smart watch, a tablet computer, a laptop computer, and the like. In embodiments, the external device can be used to set up or initialize the interface, while most or all of the processing is accomplished in the preprocessor. The preprocessor can then communicate status or actions back to the external device. In such embodiments, the external device is often a smartphone or a smartphone-connected device.

The system block diagram can include a variety of sensors that can be coupled to the interface-embedded processor. In embodiments, a microphone 330 can be coupled to the interface-embedded processor. The microphone can include an audio microphone, a transducer, or other audio pickup device suitable for audio collection. The microphone can be operated "normally on", "normally off", etc. In embodiments, the microphone can be enabled based on an output from an interface-embedded sensor. The microphone can capture audio data, speech data, and so on. In embodiments, the microphone can enable near-silent speech recognition. A barometric sensor 332 can be coupled to the interface-embedded processor. The barometric sensor can be used to determine barometric pressure with the oral cavity of the user. In embodiments, the barometric sensor can detect a tri-value state of air pressure within an oral cavity containing the interface. The tri-value state of air pressure can include nominal or ambient pressure, increased pressure, and decreased pressure. In embodiments, the tri-value state can include ambient barometric pressure, increased barometric pressure due to exhaling into a closed oral cavity, and decreased barometric pressure due to inhaling from a closed oral cavity. An ambient condition sensor 334 can be coupled to the interface-embedded processor. The ambient condition sensors can include biometric sensors. In embodiments, the biometric sensors can include temperature, heart rate, hydration, pH, oxygen, microbe, hormone, enzyme, blood pressure, jaw clenching force, and airflow sensors.

Further sensors can be coupled to the interface-embedded processor. In embodiments, a tongue position sensor (TPS) 340 can be coupled to the interface-embedded processor (or preprocessor). The TPS can be used as a tongue-based gesture interface. The TPS can detect tongue position, tongue pressure, etc. An inertial measurement unit (IMU) 342 can be coupled to the interface-embedded processor. In embodiments, one or more IMUs can be coupled. The IMU or IMUs can be used to measure jaw position, acceleration, rotation, etc. In embodiments, the TPS and the one or more IMUs can be used to accommodate situational impairment experienced by a person. Situational impairments can include high or low volume noise, poor lighting, social constraints, and so on. Situational impairments can prevent a user from reading a display, interacting with a device such as a computing device, etc. A feedback component 350 can be coupled to the interface-embedded processor. The feedback component can provide haptic feedback, audio feedback, and so on. In embodiments, the feedback can originate in the processor and can be transmitted to the interface using the wireless connectivity. The feedback can be provided based on a range of actions, to accomplish a variety of tasks, etc. In embodiments, the feedback can be responsive to active oral manipulation by a user of the interface, passive monitoring of a user of the interface, and the like.

Figure 4:
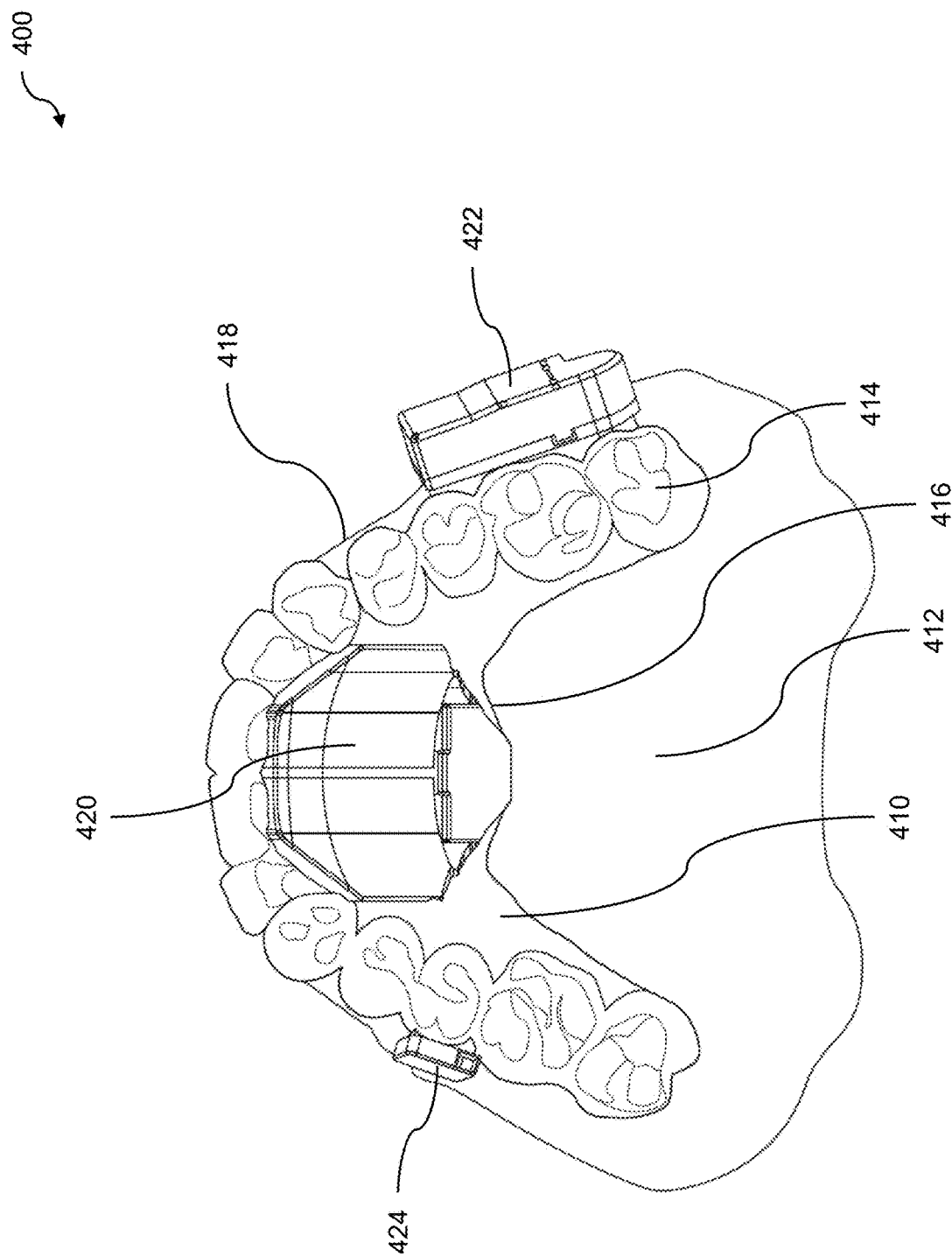
FIG. 4 illustrates an oral sensing interface.

FIG. 4 illustrates an oral sensing interface 400. The oral sensing interface 400 can take the form of a dental retainer. Sensors, inertial measurement units, tongue gesture interfaces, wireless transceivers, preprocessors, and so on, can be attached to or along a physical structure, such as a retainer, for in-mouth use. The retainer can be used by placing the retainer into the oral cavity, or mouth, of the user. The retainer, as configured to operate as an oral sensing interface, can detect tongue pressure, tongue movement, head movement, and so on. The interface, or retainer, enables data manipulation using remote augmented sensing. Wireless connectivity is provided between a processor and a wireless transceiver. The wireless transceiver is embedded in an oral sensing interface. A tongue position sensor (TPS) is coupled to the wireless transceiver, and an inertial measurement unit (IMU) is coupled to the wireless transceiver. A barometric sensor is coupled to the wireless transceiver. An additional inertial measurement unit is attached to a nonadjacent location of the interface and coupled to the wireless transceiver. Data manipulation is enabled in the processor, based on the wireless connectivity and outputs from the sensors. Data manipulation is augmented by a preprocessor coupled to the wireless transceiver.

Discussed throughout, a tongue position sensor, one or more inertial measurement units, and other sensors can be coupled to a device that can be placed into an oral cavity of a user. In embodiments, the device can include a retainer 410. The retainer 410 shown is clear and covers a palate 412 replete with teeth, such as tooth 414. The retainer 410 is illustrated by boundary edge 416 (more toward the back of the mouth) and boundary edge 418 (more toward the front of the mouth). The retainer can include a customized retainer, where the customized retainer is fitted to a particular user to ensure proper fit and to enable comfort of the user. The retainer can be fitted to cover the upper teeth or the lower teeth. A retainer covering the upper teeth may be more comfortable to a user. A retainer covering the lower teeth can enable greater motion detection, due to the anatomical mobility and freedom of movement of the lower jaw vis a vis the upper jaw. A tongue position sensor (TPS) 420 can be attached to the retainer and can be electrically coupled to a wireless transceiver unit 422. The electrical connectivity can be provided by wire traces embedded in the retainer. The wire traces can comprise serpentine shapes to allow for retainer deformation without wire breakage. In embodiments, the electrical coupling can be accomplished wirelessly. The TPS can detect tongue gestures such as tongue movement, tongue position, tongue movement speed, tongue movement acceleration, and so on. Other sensors can be coupled to the retainer. An inertial measurement unit (IMU) can be included with and coupled to wireless transceiver unit 422. The IMU can be used to determine position, acceleration, and rotation of the jaw or head of the user. In embodiments, an additional inertial measurement unit 424 can be attached to a nonadjacent location of the interface (retainer) and coupled electrically to the wireless transceiver unit 422. The unit 422 and the sensor 424 can include further sensors such as barometric pressure sensors, biometric sensors, bone-conduction microphones, bone-conduction sound generation devices, and so on. Additional sensors can be attached to the retainer at other locations along the retainer. In embodiments, pressure sensors can be embedded in or along the surface of the retainer. The pressure sensors can be used to measure pressure such as pressure resulting from clenching teeth, jaw movement such as jaw movement based on bruxism (e.g., grinding teeth), and the like.

FIG. 5A shows sensor usage. Various types of sensors, including remote sensors, are used to capture data that includes barometric data, speech data, ambient condition data, and so on. Further collected data includes tongue position sensor (TPS) data, and data collected from the one or more inertial measurement units (IMUs). The collected data can be manipulated by a processor or preprocessor, where the data manipulation uses remote augmented sensing. Wireless connectivity is provided between a processor and a wireless transceiver. The wireless transceiver is embedded in an oral sensing interface. A tongue position sensor (TPS) is coupled to the wireless transceiver, and an inertial measurement unit (IMU) is coupled to the wireless transceiver. A barometric sensor is coupled to the wireless transceiver. An additional inertial measurement unit is attached to a nonadjacent location of the interface and coupled to the wireless transceiver. Data manipulation is enabled in the processor, based on the wireless connectivity and outputs from the sensors. Data manipulation is augmented by a preprocessor coupled to the wireless transceiver.

Microphone and barometric sensor usage is shown 500. The microphone can be used to collect audio data, speech data, and so on. The microphone can include an audio microphone, a transducer, or another component suitable for providing audio data to a data manipulation system. In embodiments, the microphone enables near-silent speech recognition. The output of the microphone can include an audio signal, where the audio signal can include an analog signal, a digital signal, etc. The microphone can include one or more usage states, where the usage states can include inactive, monitoring, etc. The microphone can be operated based on actions of a user of the microphone. In embodiments, the action of the microphone can be preprogrammed.

The barometric sensor can be used to detect changes in barometric pressure within an oral cavity. The barometric sensor can include a solid state sensor, a micro-electro-mechanical system (MEMS), and so on. The output of the barometric sensor can include a signal value, code, etc. that can describe a tri-value state or any pressure value along a continuum of pressure values. In embodiments, the barometric sensor can detect a tri-value state of air pressure within an oral cavity containing the interface. The states can be represented by a value, a code, etc. In embodiments, the tri-value state can include ambient barometric pressure, increased barometric pressure due to exhaling into a closed oral cavity, and decreased barometric pressure due to inhaling from a closed oral cavity. The barometric sensor can also be used to detect tongue presses and suction gestures by sensing the pressure changes associated with such intraoral movement and manipulation. In embodiments, the barometric sensor detects pressure and pressure changes resulting from respiratory control, tongue presses, or tongue and/or mouth suction control.

Ambient sensory usage is also shown 502. An ambient conditions sensor can be used to measure and collect ambient conditions data associated with a person, such as ambient conditions within the oral cavity, biometric data, and so on. The output of the ambient conditions sensor can include changes in biometric data. As with other sensors, the ambient sensor can include states, where the states can be associated with one or more biometric parameters. The biometric parameters can include absolute values, relative values, ranges, etc. In embodiments, the biometric sensors that are used can include temperature, heart rate, hydration, pH, oxygen, microbe, hormone, enzyme, blood pressure, jaw clenching force, and airflow sensors.

Figure 5B:
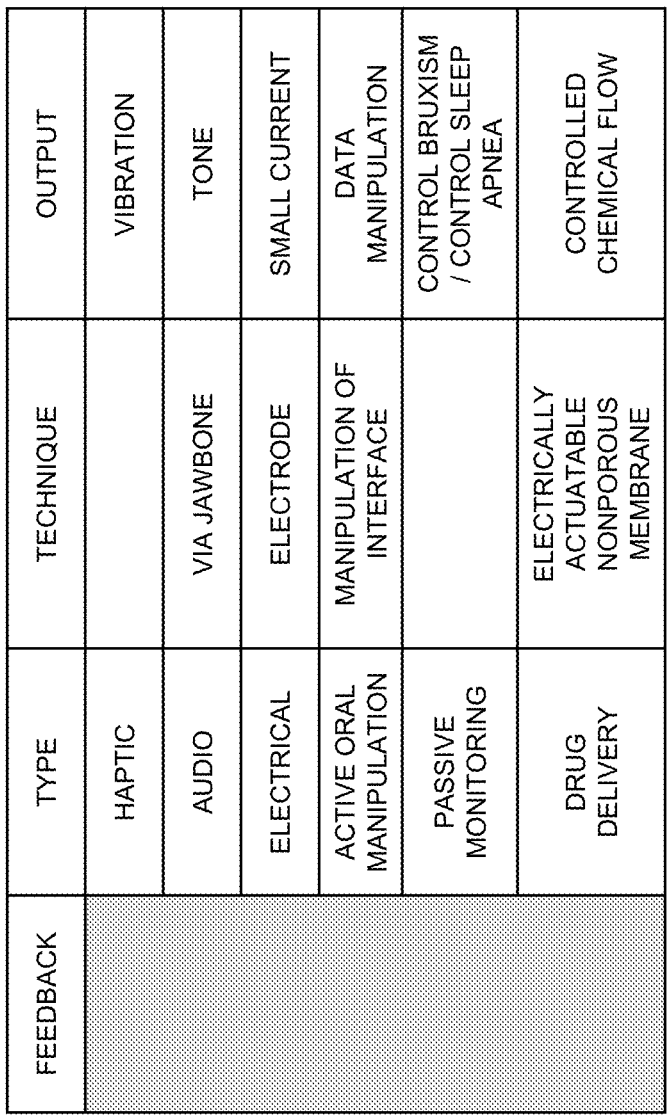
FIG. 5B shows feedback techniques.

FIG. 5B shows feedback techniques. Various types of feedback 504 can be provided to a person, where the feedback can be used to provide data, alerts, and so on. Providing feedback to a person enables data manipulation using remote augmented sensing. Various types of feedback techniques can be used to provide feedback to the person. In embodiments, a feedback technique can include haptic feedback. In embodiments, the feedback can include haptic feedback generated by a haptic device attached to the interface. The haptic feedback can include vibration, pressure, a tingling sensation, and so on. In other embodiments, the feedback can include audio feedback generated by a sound generating device attached to the interface. The audio feedback can include a tone, a live or recorded message, a series of tones or music, and the like. In embodiments, the sound generating device can use jawbone structure for audio propagation. Using jawbone structure for audio propagation provides audio feedback without an in-ear monitor, earphone, etc. The jawbone structure can include the upper jaw maxilla and frontal hard palate, or the lower jaw mandible, or a combination of both to enable audio propagation. The audio feedback can take the form of text-to-speech functionality. The feedback can include electrical stimulation by passing a small current through the soft tissue of the mouth to produce a tingling or other sensation.

In other embodiments, the feedback can be responsive to active oral manipulation by a user of the interface. The user can move their tongue, manipulate barometric pressure within an oral cavity, and so on. The oral manipulation can accomplish data manipulation in the processor. In further embodiments, feedback can include passive monitoring of a user of the interface. The passive monitoring can be used to detect and control behaviors, medical conditions, and so on. In embodiments, the feedback can be used to control bruxism or "teeth grinding" in the user. The feedback can be based on detecting clenching of teeth, jaw movement, and the like. In other embodiments, the feedback can be used to control sleep apnea in the user. Sleep apnea can be based on detecting changes in barometric pressure within the oral cavity. Feedback can be used to detect further conditions such as medical conditions, to aid in treatment of medical conditions, and so on. In embodiments, feedback can include enabling drug delivery. Drug delivery can be based on patient ambient conditions, on jaw pressure and movement, and so on. In embodiments, the drug delivery can be provided by an electrically actuatable nonporous membrane. Using the electrically actuatable nonporous membrane can enable controlled chemical flow, where the chemical flow can include drug delivery.

Figure 6:
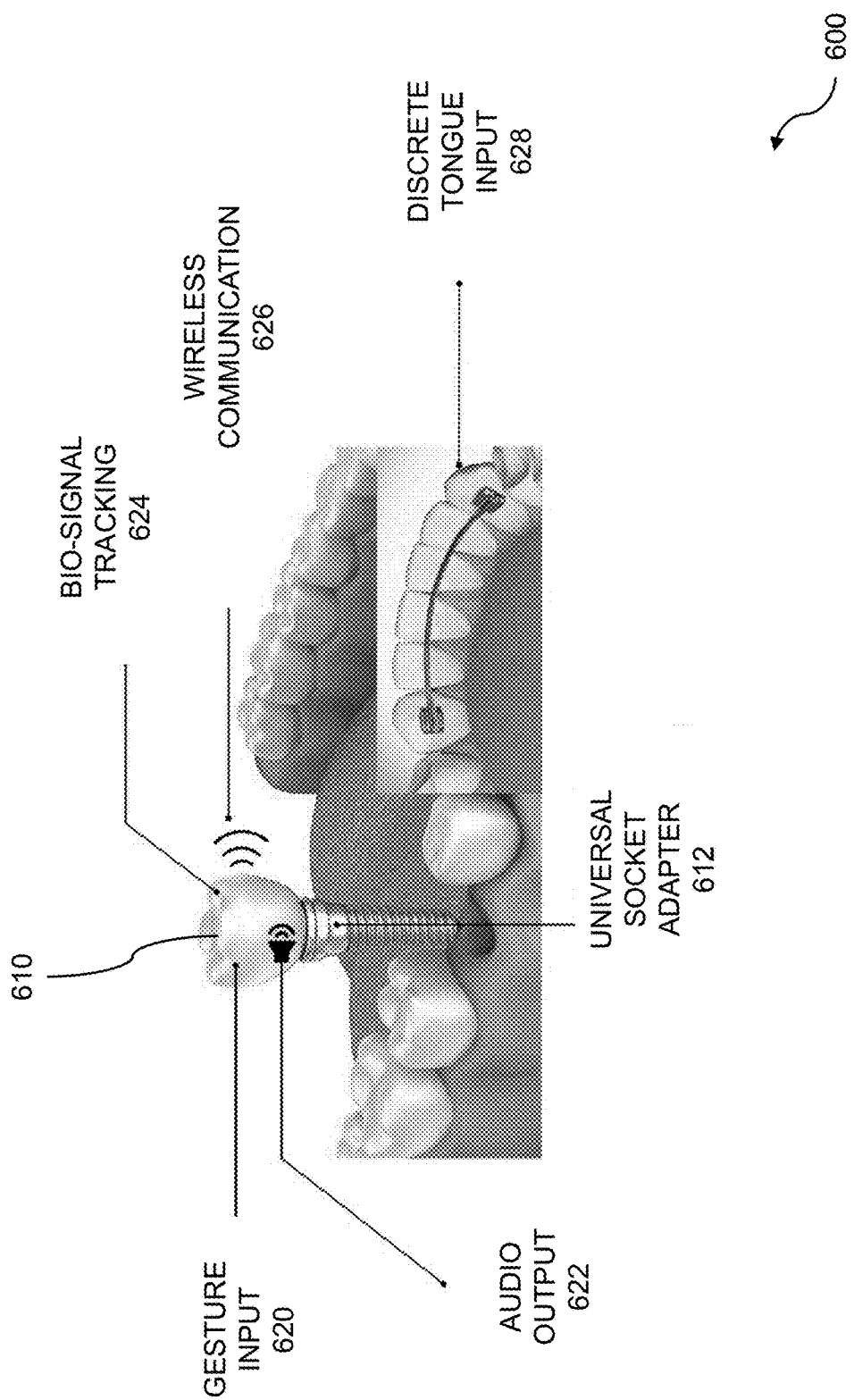
FIG. 6 illustrates a smart tooth implant.

FIG. 6 illustrates a smart tooth implant. Discussed throughout, remote augmented sensing can be used to enable data manipulation. Sensor data can be collected and feedback can be provided using wireless connectivity. The data collection, feedback provision, communications, and other enabling techniques can be accomplished using a smart tooth implant. The smart tooth implant can provide wireless connectivity between a processor and a wireless transceiver. The wireless transceiver is embedded in an oral sensing interface smart tooth. A discrete tongue position sensor (TPS) is coupled to the wireless transceiver, and a smart tooth-embedded inertial measurement unit (IMU) is coupled to the wireless transceiver. A smart tooth-embedded barometric sensor is coupled to the wireless transceiver. Data manipulation is enabled in the processor, based on the wireless connectivity and outputs from the sensors. Data manipulation is augmented by a preprocessor coupled to the wireless transceiver.

A smart tooth implant with inputs, outputs, and communication is shown 600. The smart tooth implant includes a smart tooth 610. The smart tooth implant can be substituted for an existing tooth, used to replace a missing tooth, and so on. The smart tooth can be coupled to a universal socket adapter 612. The universal socket adapter can be used to standardize implantation of the smart tooth. The smart tooth can collect input data from one or more sensors, provide feedback, enable wireless communication with a processor, and so on. The smart tooth can collect gesture input 620 data. The gesture input data can be collected from the tongue position sensor (TPS), from two or IMUs, and so on. The smart tooth can provide audio output 622. In embodiments, audio output can include audio feedback, where audio feedback can be generated by a sound generating device attached to the interface. The audio output can be received by a person using the smart tooth implant. In embodiments, the sound generating device can use jawbone structure for audio propagation. In embodiments, the smart tooth comprises a tooth partial implant, a tooth attachment, or a tooth crown. A tooth crown may replace only the upper portion of a natural tooth, but it can still include full smart tooth functionality as described herein.

The smart tooth can collect bio-signal tracking 624 data. In embodiments, an ambient condition sensor can include biometric sensors, where the biometric sensors can be used to collect the bio-signal tracking data. Various types of biometric sensors can be used to collect the bio-signal tracking data. In embodiments, the biometric sensors or "biosensors" can detect temperature, heart rate, hydration, pH, oxygen, microbes, hormones, enzymes, blood pressure, jaw clenching force, and air flow, among other bio-signals. The smart tooth can provide wireless communication 626. The wireless communication can be based on a variety of wireless communications techniques such as 802.11 Wi-Fi™, Bluetooth™, near field communication (NFC), near field magnetic induction (NFMI), ZigBee™, a wireless personal area network (WPAN), and so on. The wireless connectivity can include bidirectional communications capabilities to support data collection, to provide feedback such as audio output, and so on. The smart tooth can collect tongue input 628 data. The tongue input data can be based on a tongue position sensor discrete from the smart tooth. For example, the tongue position sensor can comprise a sensing wire along the inner surface of the front teeth, either the top set of front teeth or the bottom set of front teeth, or both. The tongue input data can augment, control, or modify data collected by, or being processed by, the smart tooth. The tongue input data can be sensed based on tongue position, tongue pressure, tongue movement, tongue movement direction, tongue movement speed, tongue movement acceleration, and so on.

Figure 7:
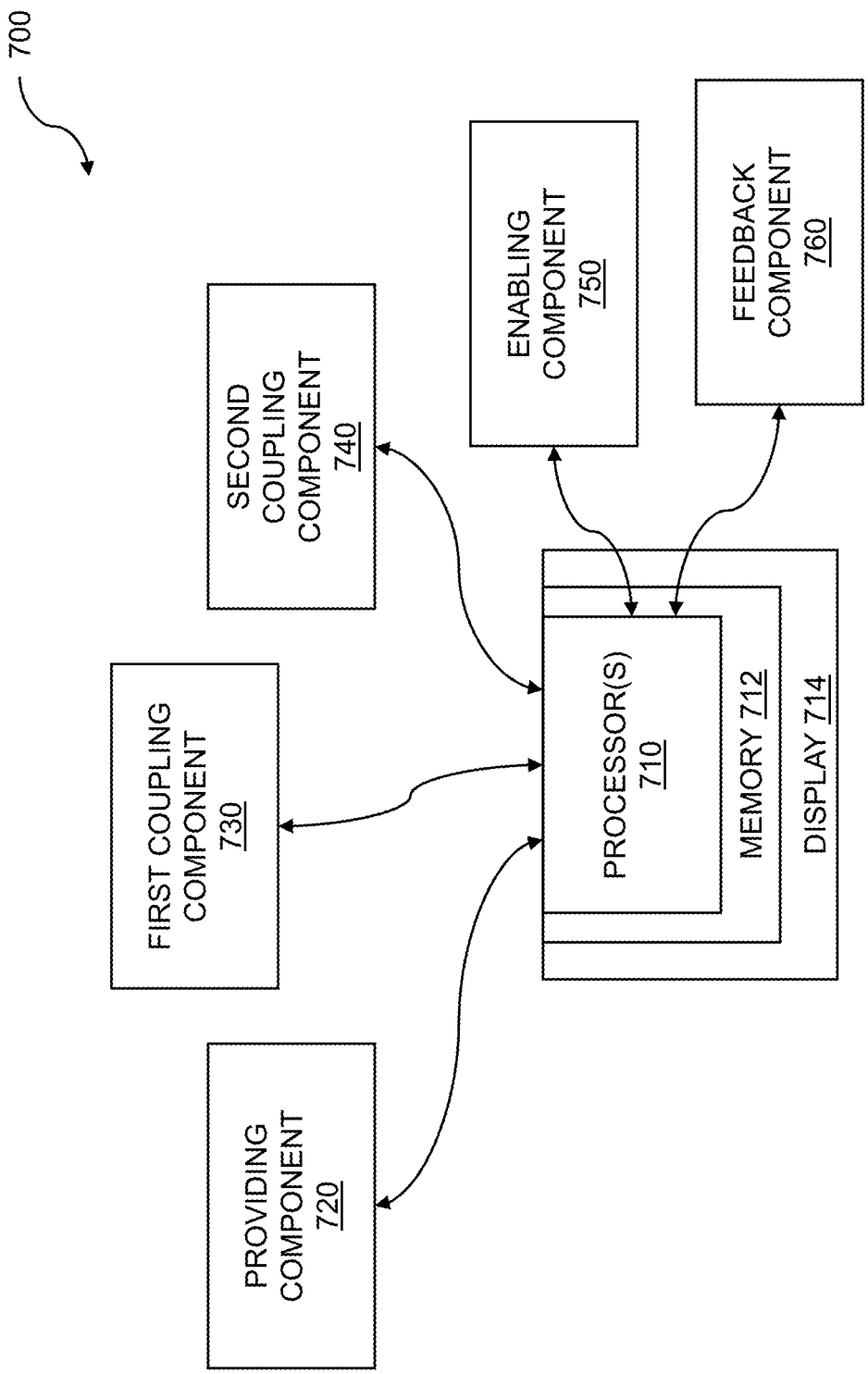
FIG. 7 is a system diagram for data manipulation.

FIG. 7 is a system diagram for data manipulation. Remote augmented sensing can be used for data manipulation, where the remote sensing can be accomplished using a barometric sensor, an ambient condition sensor, a microphone, inertial measurement units (IMUs), and so on. The sensors can be used to measure or detect a tri-value state of pressure within an oral cavity, speech including near silent speech, ambient conditions, etc. Data manipulation can further be accomplished using a prosthetic such as a retainer, where the retainer can be used to measure tongue position, pressure, and the like. In embodiments, the data manipulation can include using a smart tooth implant for wireless communication, gesture input, bio-signal tracking, audio output, etc. The augmented sensing can be used as a hands-free input and output device for data manipulation, where hands-free operation can be used by people who may not be able to use other data manipulation devices such as keyboards, mice, trackpads, etc. The augmented sensing can be used for silent, covert, or discreet data manipulation. Wireless connectivity is provided between a processor and a wireless transceiver, where the wireless transceiver is embedded in an oral sensing interface such as an implant. Data manipulation is enabled on a processor based on head movement, tongue movement, barometric pressure, speech, and so on. The system 700 can include one or more processors 710 and a memory 712 which stores instructions. The memory 712 is coupled to the one or more processors 710, wherein the one or more processors 710 can execute instructions stored in the memory 712. The memory 712 can be used for storing instructions, runtime libraries, data manipulation routines, sensor drivers, error codes or handling routines, and so on. The memory can further be used for storing sensor calibration data. Information such as sensor data can be shown on a display 714 connected to the one or more processors 710. The display can comprise a television monitor, a projector, a computer monitor (including a laptop screen, a tablet screen, a netbook screen, and the like), a smartphone display, a mobile device, or another electronic display.

The system 700 can include a computer system for data manipulation comprising: a memory which stores instructions; one or more processors coupled to the memory wherein the one or more processors, when executing the instructions which are stored, are configured to: provide wireless connectivity between a processor and a wireless transceiver, wherein the wireless transceiver is embedded in an oral sensing interface; couple a tongue position sensor (TPS) to the wireless transceiver, wherein the tongue position sensor is attached to the oral sensing interface; couple an inertial measurement unit (IMU) to the wireless transceiver, wherein the IMU is attached to a location along the oral sensing interface; and enable data manipulation in the processor, based on the wireless connectivity and outputs from the TPS and the IMU.

The system 700 can include a providing component 720. The providing component 720 can be used for providing wireless connectivity between a processor and a wireless transceiver. The wireless connectivity can be based on wireless communications standards and techniques such as 802.11 Wi-Fi™, Bluetooth™, near field communication (NFC), near field magnetic induction (NFMI), ZigBee™, a wireless personal area network (WPAN), and so on. The wireless connectivity can include bidirectional communications capabilities. In embodiments, the wireless transceiver is embedded in an oral sensing interface. The oral sensing interface can include a prosthetic device such as a retainer. The retainer can include sensors, contacts, communications components, and the like. The system 700 can include a first coupling component 730. The first coupling component 730 can be used for coupling a tongue position sensor (TPS) to the wireless transceiver, where the tongue position sensor is attached to the interface. The tongue position sensor can be used to detect a nominal position of the tongue. The tongue position sensor can be used to determine displacement of the tongue such as up or down, forward or back, left or right, and so on. The tongue position sensor can be used to measure pressure applied to the sensor by the tongue.

The system 700 can include a second coupling component 740. The second coupling component 740 can be used for coupling one or more inertial measurement units (IMUs) to the wireless transceiver, where the one or more inertial measurement units are attached to nonadjacent locations of the interface. In embodiments, functions of the first coupling component and the second coupling component are accomplished by a single coupling component. The one or more IMUs can be used to measure jaw acceleration, rotation, and so on. The one or more IMUs can be used to determine movement of the jaw within the oral cavity. The system 700 can include an enabling component 750. The enabling component 750 can be used for enabling data manipulation in the processor, based on the wireless connectivity and output from the TPS and the IMU. The data manipulation can be based on acceleration, rotation, and position of the jaw; pressure exerted by the jaw—both left side and right side; and so on. The data manipulation can be further based on barometric pressure within a closed oral cavity using a barometric sensor. In embodiments, the barometric sensor can detect a tri-value state of air pressure within an oral cavity containing the interface. The tri-value state of air pressure can be based on exhaling into the closed oral cavity to increase barometric pressure, inhaling from the closed oral cavity to reduce pressure, or a neutral pressure. In embodiments, the data manipulation can be based on voice information. The voice information can be captured using a microphone or other audio collection component coupled to a wireless transceiver. In embodiments, the microphone is enabled based an output from an embedded sensor. For example, if tongue motion, pressure, location, etc. is detected, then the microphone can be enabled. In embodiments, the microphone enables near-silent speech recognition. The microphone can also be enabled based on an additional sensor embedded onto the interface.

The system 700 can include a feedback component 760. The feedback component 760 can be used for providing feedback to a user of the interface. In embodiments, the feedback can include haptic feedback generated by a haptic device attached to the interface. The haptic feedback can include vibration, pressure, generating a tingling sensation, and so on. In other embodiments, the feedback can include audio feedback generated by a sound generating device attached to the interface. The audio feedback can include a tone or alert, speech, music, and so on. In further embodiments the feedback can originate in the processor and can be transmitted to the interface using the wireless connectivity. The audio feedback can use jawbone structure for audio propagation. The feedback, whether haptic, audio, etc., can originate in the processor and can be transmitted to the interface using wireless connectivity, where the wireless connectivity can be based on wireless connectivity techniques discussed throughout.

The system 700 can include a computer program product embodied in a non-transitory computer readable medium for data manipulation, the computer program product comprising code which causes one or more processors to perform operations of: providing wireless connectivity between a processor and a wireless transceiver, wherein the wireless transceiver is embedded in an oral sensing interface; coupling a tongue position sensor (TPS) to the wireless transceiver, wherein the tongue position sensor is attached to the oral sensing interface; coupling an inertial measurement unit (IMU) to the wireless transceiver, wherein the IMU is attached to a location along the oral sensing interface; and enabling data manipulation in the processor, based on the wireless connectivity and outputs from the TPS and the IMU.

Disclosed embodiments include an apparatus for data manipulation comprising: a wireless transceiver embedded in an oral sensing interface, wherein the wireless transceiver enables connectivity to a processor; a tongue position sensor (TPS) electrically coupled to the wireless transceiver, wherein the tongue position sensor is attached to the oral sensing interface; and one or more inertial measurement units (IMUs) electrically coupled to the wireless transceiver, wherein the one or more inertial measurement units are attached to locations along the oral sensing interface.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited neither to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A processor-implemented method for data manipulation comprising:
providing wireless connectivity between a processor and a wireless transceiver, wherein the wireless transceiver is embedded in an oral sensing interface, wherein the oral sensing interface detects tongue gestures;
coupling a tongue position sensor (TPS) to the wireless transceiver, wherein the tongue position sensor is attached to the oral sensing interface;
coupling an inertial measurement unit (IMU) to the wireless transceiver, wherein the IMU is attached to a location along the oral sensing interface;
coupling an interface-embedded barometric sensor to the wireless transceiver, wherein the barometric sensor detects a penta-value state of air pressure within an oral cavity containing the interface; and
enabling data manipulation in the processor, based on the wireless connectivity, the barometric sensor, and outputs from the TPS and the IMU.

2. The method of claim 1 further comprising coupling an interface-embedded preprocessor to the wireless transceiver to augment the enabling data manipulation.

3. The method of claim 1 wherein an output of the barometric sensor is used in the enabling data manipulation.

4. The method of claim 1 wherein the barometric sensor detects a continuum of barometric pressures.

5. The method of claim 1 further comprising coupling an interface-embedded temperature sensor to augment the barometric sensor.

6. The method of claim 1 further comprising coupling at least one additional inertial measurement unit to the wireless transceiver.

7. The method of claim 6 wherein the inertial measurement unit and the at least one additional inertial measurement unit are attached to nonadjacent locations along the interface.

8. The method of claim 6 wherein the enabling data manipulation is augmented by the at least one additional inertial measurement unit.

9. The method of claim 1 further comprising providing feedback to a user of the interface.

10. The method of claim 9 wherein the feedback is responsive to passive monitoring of the user of the interface.

11. The method of claim 1 further comprising coupling an ambient condition sensor to the wireless transceiver.

12. The method of claim 1 further comprising coupling one or more biometric sensors to the wireless transceiver.

13. The method of claim 1 wherein the data manipulation is used to accommodate impairment experienced by a person.

14. The method of claim 1 wherein the data manipulation is used to provide input for an augmented reality system used by a person.

15. The method of claim 1 further comprising coupling an interface-embedded microphone to the wireless transceiver, wherein the microphone is enabled based on output from the TPS.

16. The method of claim 15 wherein the microphone is enabled based on an output from an interface-embedded sensor.

17. The method of claim 1 further comprising coupling a bone-conduction sound generating device to the interface.

18. The method of claim 1 further comprising coupling a battery to the wireless transceiver.

19. The method of claim 18 wherein the battery is charged wirelessly in a user's oral cavity.

20. The method of claim 1 wherein the TPS enables oral mouse function detection.

21. The method of claim 1 further comprising coupling one or more light-emitting diodes to the wireless transceiver.

22. The method of claim 1 wherein the oral sensing interface further detects tongue pressure.

23. The method of claim 1 wherein the TPS senses tongue movement speed.

24. The method of claim 1 further comprising coupling the IMU to the processor, wherein the coupling is accomplished utilizing a serpentine connection.

25. The method of claim 1 further comprising coupling a jaw clenching force sensor to the wireless transceiver to augment the enabling data manipulation.

26. The method of claim 1 further comprising associating the penta-value state with a code word.

27. The method of claim 1 wherein the tongue position sensor detects an expression of three-dimensional movement by the tongue.

28. The method of claim 1 wherein the TPS senses tongue movement acceleration.

29. A computer system for data manipulation comprising:
a memory which stores instructions;
one or more processors coupled to the memory wherein the one or more processors, when executing the instructions which are stored, are configured to:
provide wireless connectivity between a processor and a wireless transceiver, wherein the wireless transceiver is embedded in an oral sensing interface, wherein the oral sensing interface detects tongue gestures;
couple a tongue position sensor (TPS) to the wireless transceiver, wherein the tongue position sensor is attached to the oral sensing interface;
couple an inertial measurement unit (IMU) to the wireless transceiver, wherein the IMU is attached to a location along the oral sensing interface;
couple an interface-embedded barometric sensor to the wireless transceiver, wherein the barometric sensor detects a penta-value state of air pressure within an oral cavity containing the interface; and
enable data manipulation in the processor, based on the wireless connectivity, the barometric sensor, and outputs from the TPS and the IMU.

30. An apparatus for data manipulation comprising:
a wireless transceiver embedded in an oral sensing interface, wherein the wireless transceiver enables connectivity to a processor, wherein the oral sensing interface detects tongue gestures;
a tongue position sensor (TPS) electrically coupled to the wireless transceiver, wherein the tongue position sensor is attached to the oral sensing interface;
an interface-embedded barometric sensor coupled to the wireless transceiver, wherein the barometric sensor detects a penta-value state of air pressure within an oral cavity containing the interface; and
wherein the data manipulation is based on one or more inertial measurement units (IMUs) electrically coupled to the wireless transceiver and the barometric sensor, wherein the one or more inertial measurement units are attached to locations along the oral sensing interface.

* * * * *

UNITED STATES PATENT AND TRADEMARK OFFICE
CERTIFICATE OF CORRECTION

| | |
|---|---|
| PATENT NO. | : 11,941,161 B2 |
| APPLICATION NO. | : 17/366186 |
| DATED | : March 26, 2024 |
| INVENTOR(S) | : Tomas Alfonso Vega Galvez and Corten Singer |

It is certified that error appears in the above-identified patent and that said Letters Patent is hereby corrected as shown below:

On the Title Page

The line below "(12) United States Patent", the last name reads "Galvez et al." but it should read "Vega Galvez et al."

Item (72) the first inventor's last name reads "Galvez" but it should read "Vega Galvez"

Signed and Sealed this
Third Day of September, 2024

Katherine Kelly Vidal
*Director of the United States Patent and Trademark Office*